United States Patent [19]

Kim et al.

[11] Patent Number: 5,975,905
[45] Date of Patent: Nov. 2, 1999

[54] CERAMIC SLURRY COMPOSITION FOR CERAMIC CORE OF A DENTAL PROSTHESIS

[76] Inventors: Dae Joon Kim, Misung Apt. B-803, Yoido-Dong, Yongdungpo-ku, Seoul, Rep. of Korea; Myung Hyun Lee, Daemyung Apt. 206-504, Daehwa-Dong, Ilsan-Ku, Koyang, Kyungki-Do, Rep. of Korea

[21] Appl. No.: 09/018,643

[22] Filed: Feb. 4, 1998

Related U.S. Application Data

[62] Division of application No. 08/850,322, May 2, 1997, Pat. No. 5,776,382.

[30] Foreign Application Priority Data

Aug. 31, 1996 [KR] Rep. of Korea ................ 96 37493

[51] Int. Cl.⁶ ..................................................... A61C 5/08
[52] U.S. Cl. ........................................................ 433/222.1
[58] Field of Search ..................................... 433/218, 219, 433/222.1, 223

[56] References Cited

U.S. PATENT DOCUMENTS

| | | | |
|---|---|---|---|
| 4,585,417 | 4/1986 | Sozio et al. | 264/19 |
| 4,772,436 | 9/1988 | Tyszblat | 264/19 |
| 5,346,397 | 9/1994 | Braiman | 264/19 |
| 5,453,227 | 9/1995 | Rieger | 264/19 |

*Primary Examiner*—Nicholas D. Lucchesi
*Attorney, Agent, or Firm*—Marshall, O'Toole, Gerstein, Murray & Borun

[57] ABSTRACT

An improved method for simplifying a slip casting applied conventional all ceramic core molding process by molding an all ceramic core from a ceramic sheet. In the method, there is prepared a slurry which consists mainly of alumina, spinel, alumina/zirconia powder, by adding thereto a dispersant, a binding agent, a plasticizer, a solvent and the like. The slurry is formed into a sheet having a thickness of 0.1 mm to 1.0 mm for thereby fabricating a tooth molding mass by using a heat hydrostatic pressing at a pressure of 15 Kgf/cm² to 150 Kgf/cm² at a temperature of 50° C. to 110° C., with slurry composition for fabricating an all ceramic jacket crown applicable to an artificial crown.

2 Claims, No Drawings

CERAMIC SLURRY COMPOSITION FOR CERAMIC CORE OF A DENTAL PROSTHESIS

CROSS-REFERENCE TO RELATED APPLICATION

This application is a divisional of U.S. application Ser. No. 08/850,322, filed May 2, 1997, now U.S. Pat. No. 5,776,382.

BACKGROUND OF THE INVENTION

1. Field of the Invention

The present invention relates to a method of fabricating an all ceramic jacket crown which is placed over a decayed or broken tooth so that the original shape and function of such tooth is restored, wherein the ceramic tooth core is made by an innovative method.

2. Description of Prior Art

Conventionally, tooth crowns used for restoring decayed or broken teeth can be classified into metal ceramic crown and all ceramic jacket crown, depending upon the materials employed.

The artificial crown now widely in use is a metal ceramic crown, more specifically a PFM (porcelain fused metal) crown which is manufactured by melting a ceramic powder on a metallic crown formed of a precious metal core such as gold, silver, platinum or palladium so as to produce a natural tooth color appearance. However, the conventional metal ceramic crown is disadvantageous because of its low esthetic quality and due to side effects and sensitiveness caused by the metallic material employed therein.

A ceramic artificial crown, that is, an all ceramic jacket crown comprises single crown and a tooth mold formed of a ceramic material and is attached to an appropriately prepared tooth substance. Unlike a metal ceramic crown, the color of the all ceramic jacket crown may be easily adjusted to match that of a natural tooth to thereby exhibit a high esthetic quality and accordingly is welcome by many relevant experts due to its biological compatibility and in addition, virtually no side effects have been observed.

An all ceramic jacket crown as described above has many advantages relative to a metal ceramic tooth crown, and a variety of ceramic materials and fabrication steps thereof have been developed based on continued research in an effort to replace the conventional metal ceramic crown. Yet, the characteristically low fracture toughness and low physical strength of ceramics are obstacles in the development of all ceramic jacket crowns.

To solve the above problems, an improved fabrication method of an all ceramic jacket crown having high durability has been introduced. According to U.S. Pat. No. 4,772,436 of Sep. 20, 1988, a slip casting method is disclosed wherein, alumina by itself or a mixture formed by adding a considerable amount of zirconia to alumina is used as a ceramic source material. To make the slip of this method, 12~20 g of water is added to 100 g of metal oxide powder and 0.05~0.5 g of a stabilizer such as polyvinyl alcohol, acrylic acid, cellulose ester or sodium silicate is added thereto. An acid such as citric acid is added to control the pH of the slip. Prior to its use, the slip is subjected to an ultrasonic treatment under a vacuum state to eliminate bubbles therefrom and then a base structure is formed by coating the slip on a tooth mold which contracts during heat treatment, allowing the formed structure to be easily removed therefrom.

The tooth mold is formed of calcium sulfate hemihydrate ($CaSO_4 \cdot \frac{1}{2}H_2O$) having an expansion rate of 0.1~0.4%, and also may be formed of a mixture of a refractory material such as alumina or silica, and a binding agent such as sodium silicate, ethyl silicate, ammonium sulfate or ammonium acid phosphate. Metallic oxide particles coated on the tooth mold form an infrastructure having a pore-like structure which is formed through a first sintering, and the infrastructure exhibits a contraction rate of less than 0.4% and yet maintains the desired precision by offsetting the dry expansion effects which occurred during the preceding tooth mold fabrication step.

When applied to 3.5 $\mu$m particles, the first sintering is carried out at a temperature of 1,050° C.~1,150° C. for one to three hours, and sintering contraction is minimized by the rapid rate of temperature elevation. Glass impregnation, in which glass is impregnated into the infrastructure obtained by the first sintering, is performed at a similar temperature to that of the first sintering for less than two to four hours so as to prevent contraction resulting from the impregnation, thereby not influencing the structure formed as a result of the first sintering.

Oxides such as boron oxide, lead oxide and vanadium oxide are added to increase the wettability in the glass composition. Oxides such as boron oxide, lead oxide and a lanthanum oxide are added to lower viscosity. Also, the reactivity of the glass with regard to the metal oxide must be neither too strong nor too weak, thus a glass powder which contains alumina or zirconia in an amount slightly less than the saturation of glass vis-a vis those metal oxide at the impregnation temperature is employed. The heat expansion coefficient of glass should be a little less than that of the first-sintered oxide frame structure to allow heat impact resistance of the tooth crown. The heat expansion coefficient of glass is increased when a sodium oxide, a calcium oxide or a lithium oxide is added thereto, but decreased when a silicon oxide or a titanium oxide is added thereto. Here, the weight percentages of the major components of glass are, $SiO_2$:20, $B_2O_3$:19, $Al_2O_3$:20, $La_2O_3$:30, $CaO$:5, $TiO_2$:4, and pigment oxide:2.

To impregnate glass into the metal oxide skeleton, glass paste which, when heated to the appropriate temperature, melts and spreads spontaneously inside the entire volume of the infrastructure by filling all of the pores, can be applied on the outer surface of the infrastructure of the tooth prosthesis. In order to prevent the variations in the surface structure caused by the remaining glass, the prosthesis which comes into contact with the tooth should not contact the melted glass and that the filling of the pores located in the vicinity of this surface is effected by capillarity starting from the interior of the infrastructure mass of fritted metal oxide particles.

The structure formed after glass impregnation is treated by one or two enamel layers, thereby obtaining the desired optical characteristics, a variety of colors and resulting in an appearance that is similar to a natural tooth.

To form a ceramic core by a slip casting method, a slip should first be manufactured and a stabilizer should be added thereto for stability, and an ultrasonic treatment has to be applied to make the mixture of the slip to be uniform. The thusly obtained stable and uniform slip is coated on a plaster mold of a tooth using a brush, then dried and sintered at around 1,150° C., and carved out by a knife so that the thickness is adjusted to correspond to the plaster tooth mold. Then, a tooth core is manufactured by impregnating a glass powder into the first-sintered portion. The process for stabilizing, uniformly mixing and drying the slip and for appropriately carving the slip cast to obtain the desired constant core thickness requires a long time and many fabrication steps, and thus, is quite expensive.

SUMMARY OF THE INVENTION

While conducting research to solve the problems encountered in the prior art, the inventors of the present invention have discovered an innovative all ceramic jacket crown which has excellent effects yet requires only a simple fabrication method. The method of making a ceramic sheet for a ceramic tooth core casting in accordance with the present invention includes the steps of: forming a ceramic slurry mixture by mixing a known metal oxide powder, a solvent, a dispersant, a binding agent and a plasticizer at a proper mixing rate; degassing the slurry to eliminate bubbles therefrom so as to increase its viscosity; casting for forming a ceramic sheet having a certain thickness; and drying the resultant to remove the solvent. The completed sheet is cut, unified, sintered and impregnated with glass, thereby forming the desired ceramic tooth core.

The present invention solves the above-described conventional problems confronted at dental laboratories by using a simplified core fabrication technique when manufacturing an all ceramic tooth jacket crown, by shaping the core using a ceramic sheet formed in accordance with the present invention. To eliminate the many steps needed for making a conventional tooth crowns which requires the fabrication of a new slip each time a new crown is made, the present invention employs a ceramic sheet to simplify the core fabrication process in making tooth crowns and the fabrication of highly precise tooth crowns is possible because the need of many fabrication steps and possible errors associated therein are advantageously eliminated, thereby simplifying the overall fabrication process and the desired characteristics are stably maintained for the thusly fabricated ceramic cores of all ceramic tooth crowns.

The all ceramic jacket crown fabrication method according to the present invention includes the steps of: forming a slurry by mixing a metallic oxide selected from a particle-type alumina or a spinel (MgO. $Al_2O_3$) by itself or a powder mixture of alumina and zirconia, 0.5 wt. % to 2.0 wt. % of a dispersant based on the weight of the metallic oxide, 30 wt. % to 90 wt. % of a solvent based on the weight of the metallic oxide, 5 wt. % to 12 wt. % of a binding agent based on the weight of the metallic oxide, and 7 wt. % to 17 wt. % of a plasticizer based on the weight of the metallic oxide; degassing the slurry; forming the degassed slurry into a ceramic sheet having a thickness of 0.1 mm to 1.0 mm by using a doctor blade method or a roll compaction method; coating the ceramic sheet onto a tooth-shaped gypsum mold which has been heated at a temperature of 100~200° C. for more than 10 minutes for dehydration; attaching the sheet and the gypsum mold by applying thereto a pressure of 15~150 Kgf/cm$^2$ for 5 to 15 minutes while heating the gypsum mold coated with the ceramic sheet at a temperature of 50~110° C.; fabricating a sintered body by heating at a temperature elevation speed of 1° C./min until 500° C. is reached, and at a temperature elevation speed of 3° C./min until 1150° C. is reached; and coating a glass powder onto the sintered body and heating the same

DETAILED DESCRIPTION OF THE INVENTION

According to the present invention, the metallic oxide used in making the ceramic sheet which is easily castable, comprises a particle-type alumina or a spinel (MgO. $Al_2O_3$) by itself, or a mixed powder of alumina and yttria stabilized zirconia which has three moles of yttria mixed with zirconia, wherein the alumina particles may be replaced with alumina fibers instead. The average particle diameter of the alumina powder ranges from 3 μm to 10 μm having more than 99.5% purity. Such alumina can be used alone or as a mixed powder wherein yttria stabilized zirconia having an average particle diameter of 0.25 μm and a purity of 99.9% or more is added up to 10 to 40 wt. %, for improving the low durability of the first sintered body employed. To achieve the same purpose, a rare earth metal oxide such as cerium oxide or a transitional metal oxide such as niobium oxide may be used along with yttria.

To fabricate a ceramic sheet that is made to be highly uniform by preventing clustering and by widely dispersing the ceramic powder, and having a high filling density, KD-1 (a brand name of the ICI company of England) which is a copolymer of polyester and polyamine, is used as the dispersant. Also, depending upon the average particle diameter and the surface conditions of the ceramic powder, menhaden oil, phosphate ester and glycerol trioleate may be employed as well. To satisfy the above conditions, the amount of added dispersant against the metal oxide is preferably in the range from 0.5~2.0 weight percent. That is, if the amount is less than the above range, the metal oxide is difficult to disperse, and if the amount is greater than this range, the dispersant causes the powder particles to aggregate and results in quality degradation.

In fabricating the ceramic sheet, a binding agent is employed to bind each of the metal oxide particles, to improve the physical durability of the ceramic sheet and to prevent the ceramic sheet from being easily cracked or bent.

In the present invention, polyvinyl butyral (i.e., PVB 79, which is a brand name of the Monsanto Company of the U.S.A.) is employed as the binding agent, but a polyvinylic or an acrylic polymer may also be used instead. The amount of the added binding agent according to the present invention is preferably in the range from 5 to 12 weight percent against the metal oxide, and if the added amount is less than this range, the metal oxide loses its binding strength. On the other hand, if the added amount exceeds the above range, the powder binding strength increases but the density decreases after sintering.

In general, a plasticizer denotes an organic compound having a high molecular weight which is used to facilitate a casting process by providing plasticity to the polymer to thereby lower the polymer viscosity, and in the present invention, a plasticizer is employed to give flexibility to the ceramic sheet and improving its workability. Here, BBP (benzyl butyl phthalate), or DBP (dibutyl phthalate) is used as the plasticizer, but a general plasticizer which is well known to a macromolecular industry may be used instead. An example of a general plasticizer would be phthalate, which is employed in the present invention, while other phthalate polymers, glycol polymers or phosphate polymers may also be used. The amount of the plasticizer added to the present invention is preferably within the range of 7 to 17 weight % against the metal oxide, because an amount less than such range is insufficient for providing plasticity to the binding agent, while an amount that is greater than such range would undesirably lower the sintering density of the core. Thus, to improve the durability and workability characteristics of the ceramic sheet, a binding agent and a plasticizer are added thereto. However, too much plasticizer decreases the total amount of ceramic material in the fabricated ceramic sheet causing the sintering density of the core to decrease, thereby corrupting the core type during the glass powder impregnating process which is done after sintering.

A solvent is required to dissolve organic materials such as the plasticizer and the binding agent, and such solvent may be one or a mixture of the following materials: a ketone group such as dimethyl ketone, diethyle ketone, MEK (methyl ethyl ketone), diethyleketone, and MIBK (methyl isobuthyl ketone); a halide such as TCE (trichloroethylene), dichloroethylene, and monochloroethylene; an alcohol group having less than five carbons such as methanol, ethanol, propanol, and butanol; and an aromatic compound such as benzene, toluene, xylene and chlorobenzene. A compound solvent formed by mixing 70 weight % of MEK and 30 weight% of ethanol, and a 70 weight % of TCE and 30 weight % of ethanol compound solvent are preferably used in the present invention. The volatility of a compound solvent restricts any sudden evaporation of the solvent, thereby preventing the formation of pores on the surface of the ceramic sheet during the drying process. The amount of added solvent is preferably within the range of 30 to 90 weight % against the metal oxide. If the amount of solvent exceeds the above-mentioned range, the degassing process requires a long time and also the alumina/zirconia compound powder having a large difference in specific gravity between the two components therein, causes agglutinations due to segregation during the mixing process. Meanwhile, if the added solvent is less than the above-mentioned range, a milling efficiency decreases and accordingly there are difficulties in performing the degassing process and undesired bubbles may still remain within the ceramic sheet. Therefore, to maintain the desired viscosity of the slip during the degassing and mixing steps in forming the ceramic sheet, the amount of solvent should be adjusted according to the respective amounts of powder and organic matter being added thereto. The amount of added solvent is 30~90 weight % against the metal oxide, and more preferably, 40~60 weight %.

In the slurry which acts as the ceramic slip manufactured through a ball mill mixing process, air is introduced therein during the mixing process and bubbles due to the vapor pressure of the solvent are formed therein as well. These bubbles, if not removed prior to the ceramic sheet casting process, may cause the ceramic sheet to crack or bend, thereby deteriorating the physical property of the overall ceramic sheet. Thus, all bubbles should be removed in order to manufacture a ceramic sheet having the desired characteristics, and a degassing process using a vacuum pump (vacuum capacity: 50 L/min, vacuuming time: 20~90 min) is employed to remove the bubbles. At this time, the slurry is agitated at a constant rate of 250 rpm for uniform degassing. During the degassing process of the slurry, the evaporation of the solvent as well as the bubbles in the slurry occurs at the same time, thereby affecting the viscosity of slurry. Controlling the viscosity of the slurry is a crucial factor in obtaining the desired ceramic sheet, thus the viscosity is measured at predetermined intervals by using a Brookfield viscometer and casting is performed when the viscosity ranges from 8,000 to 30,000 cP.

The degassed alumina and alumina/zirconia ceramic slurry is cast into a sheet by using an automatic doctor blade apparatus. A carrier film coated by silicon resin and having a thickness of 100 $\mu$m is preferably used as the ceramic sheet conveying film, whereby the film has a clean surface, is flexible and does not react to an organic additive. The thickness of the ceramic sheet is controlled by a first and second micrometer attached to the blade apparatus.

The ceramic sheets can be manufactured by a doctor blade method or a roll compaction method by using a known ceramic sheet fabricating machines. The thickness of the ceramic sheet which may be controlled depending on its use, is formed to be within 0.1 to 1.0 mm in the present invention. Consequently, any additional treatments for adjusting the thickness of the tooth crown after casting the tooth core is not required.

An appropriately cut ceramic sheet is attached to a tooth mold formed of a heat-treated plaster so as to form a tooth profile. Prior to casting the ceramic sheet in the plaster mold, the plaster mold should be heat-treated at a temperature ranging from 100° C. to 200° C. to evaporate any moisture within the plaster; other wise the moisture which evaporates from the plaster would not pass through the ceramic sheet because bubbles may form in the ceramic sheet due to the evaporated moisture, resulting in undesired imperfections on the ceramic sheet surfaces which are in contact with the plaster, and therefore the desired ceramic crown may not be obtained after sintering.

The adhesion between the ceramic sheets coated on the plaster mold is not thorough enough and there are spaces between the sheet and the plaster mold due to the partial contact therebetween. Therefore, in order for the coated ceramic sheet to have a tooth profile that matches the contour of the plaster mold, a heat hydrostatic pressing is applied to the ceramic sheet by using a liquid such as oil or water as a pressure transferring medium. The heat and pressure applied to the ceramic sheet enhances the flexibility of the ceramic sheet, improves the pressing effect to thereby accelerate and reinforce the bonding between the ceramic sheets, and tightly attaches the ceramic sheet to the plaster mold, thereby desirably casting an accurate profile of the tooth mold. Before the heat hydrostatic pressing process is applied to the ceramic sheet, the plaster mold having the ceramic sheet coated thereon is inserted into a rubber bag to prevent any contacting with liquid or moisture, and a vacuuming apparatus is used to evacuate the air therein so that the rubber bag tightly encloses the plaster mold having the ceramic sheet thereon according to the shape thereof. During the heat hydrostatic pressing step, a temperature and pressure which are sufficient enough to generate a complete bonding on the contact surface and the plaster mold surface must be applied so that the organic materials added to the ceramic sheet attain the desired fluidity to allow a condensed structure thereof. The casting conditions for the plaster mold and the ceramic sheet include sufficient pre-heating at a temperature ranging from 50 to 110° C. under a pressure of 15 to 150 Kgf/cm$^2$, pressing, and then pressurized heating for 5 to 15 minutes.

After the heat hydrostatic pressing step, the plaster mold with the ceramic sheet thereon is removed from the rubber bag and the ceramic sheet cast coated on the gypsum mold is slowly heated at less than 1° C./min and the temperature is increased until 500° C. is reached, then each adduct in the organic material becomes volatile and heated at 3° C./min and the temperature is increased until 1150° C., thereby fabricating a first sintering agent for a tooth core. During a first sintering, the tooth mold formed of calcium sulfate hemihydrate contracts and is therefore easily detached from the sheet sintering body. The above method has been previously referred to as a conventional technique under which a contraction due to dehydration occurs during a drying process of a frame structure and a sintering process. In the present invention, however, a dehydrated plaster mold is used prior to coating a ceramic sheet onto the plaster mold. Therefore, a ceramic tooth core fabrication method has conformed to a melting impregnation process in which a known glass powder is spread on a first-sintered body and heated.

As described above, concerning U.S. Pat. No. 4,772,436, a preparation for a ceramic powder suspension and a thickness controlling of a casted core ought to occur in a dental laboratory, whereby it takes a longer time to manufacture a pure ceramic tooth crown while incurring a high cost.

However, the present invention enables a ceramic sheet having a constant thickness to be cast into a ceramic tooth crown, thus to facilitate and simplify the fabrication process of the ceramic tooth crown, and accordingly it is expected to be widely applied to practical use compared to the conventional metal-ceramic tooth crown. Further, a reduced cost will lead to an increased consumption while providing users with greater convenience.

The present invention will be further described in the accompanying examples but is not limited thereto.

EXAMPLE 1

Alumina Sheet Fabrication

A compound solvent formed of 70 weight % of methyl ethyl ketone and 30 weight % of ethanol and a dispersant KD-1 were added to $Al_2O_3$ powder having more than 99.5% purity and an average particle diameter of $3\mu m$ and which were then placed, for a first mixture, into an alumina ball mill which in turn was mixed at ordinary temperature for 6 hours and at a condition of 130 rpm. To the above mixture there were also added, for a second mixture, poly vinyl butyral as a binding agent and dibutyl phthalate as a plasticizer at 130 rpm for 18 hours to there by manufacture a slurry which constituents are indicated in the accompanying table.

| Constituent | Addition amount (g) |
| --- | --- |
| alumina | 100 |
| dispersant | 0.75 |
| binding agent | 10 |
| plasticizer | 12.5 |
| solvent | 50 |

When the mixture was completed, bubbles generated internally or externally were removed by using, for 30 minutes, a vacuum pump having a capacity of 50 L/min. To decrease a large solvent content added to the mixture so as to facilitate mixing and dispersion, a debubbling process of the slurry was carried out at a speed of 250 rpm. The molding conditions of the slurry and characteristics after the molding are as follows.

| Properties | | Example 1 |
| --- | --- | --- |
| casting rate (cm/min) | | 30 |
| blade height (mm) | | 1.3 |
| viscosity | | 12000 |
| greensheet | left end | 0.66 |
| thickness (mm) | middle | 0.65 |
| | right end | 0.66 |
| appearance inspection | | no faults |
| bending or cracking at skim | | none |
| bending or cracking at sinter | | none |

EXAMPLE 2

Alumina/Zirconia Sheet Fabrication

For a first mixture, a yttria stabilized zirconia was added in a weight ratio of 27% against the entire powder to a solution including a compound solvent formed of methyl ethyl ketone and ethyl alcohol, and including a dispersant KD-1, to thereby pulverize and evenly disperse the aggregation. For a second mixture, an alumina powder having more than 99.5% purity and an average particle diameter of $3\mu m$ was mixed to the first mixture under a volume ratio of 73% against the entire powder. For a third mixture, poly vinyl butyryl as a binding agent and dibutyl phthalate were added to the even mixture of alumina and zirconia. The constituents are shown in the accompanying table.

| Constituent | Addition amount (g) |
| --- | --- |
| alumina | 80 |
| zirconia | 30 |
| dispersant | 0.77 |
| binding agent | 10 |
| plasticizer | 12.5 |
| solvent | 50 |

The slurry forming conditions and properties are as follows.

| Properties | | Example 1 |
| --- | --- | --- |
| casting rate (cm/min) | | 30 |
| blade height (mm) | | 1.45 |
| viscosity | | 15000 |
| greensheet | left end | 0.56 |
| thickness | middle | 0.57 |
| (mm) | right end | 0.56 |
| appearance inspection | | no faults |
| bending or cracking at skim | | none |
| bending or cracking at sinter | | none |

EXAMPLE 3

Alumina Sheet Fabrication

A compound solvent formed in a weight ratio of 7:3 of trichloro ethylene to ethanol and a dispersant KD-1 were added to $Al_2O_3$ powder having more than 99.5% purity and an average particle diameter of 3 $\mu m$ and these were then placed, for a first mixture, into an alumina ball mill which in turn was mixed at an ordinary temperature for 6 hours and under a condition of 130 rpm. To the first mixture there were also added, for a second mixture, poly vinyl butyryl as a binding agent and benzyl butyl phthalate as a plasticizer at 130 rpm for 18 hours to there by manufacture a slurry which constituents are shown in the accompanying table.

| Constituent | Addition amount (g) |
| --- | --- |
| alumina | 100 |
| dispersant | 0.7 |
| binding agent | 8 |
| plasticizer | 10 |
| solvent | 50 |

The slurry forming conditions and properties areas follows.

| Properties | | Example 1 |
| --- | --- | --- |
| casting rate (cm/min) | | 30 |
| blade height (mm) | | 1.3 |
| viscosity | | 16000 |
| greensheet | left end | 0.64 |

| Properties | Example 1 |
| --- | --- |
| thickness (mm) middle | 0.63 |
| right end | 0.64 |
| appearance inspection | no faults |
| bending or cracking at skim | none |
| bending or cracking at sinter | none |

EXAMPLE 4
Alumina/Zirconia Sheet Fabrication

For a first mixture, a yttria stabilized zirconia 3Y-TZP was added in a weight ratio of 39% against the entire powder to a solution including a compound solvent formed of methyl ethyl ketone and ethyl alcohol and including a dispersant KD-1, to thereby pulverize and evenly disperse the aggregation. For a second mixture, an alumina powder having more than 99.5% purity and an average particle diameter of 3 μm was mixed to the first mixture under a volume ratio of 61% against the entire powder. For a third mixture, poly vinyl butyryl was added as a binding agent and dibutyl phthalate to the even mixture of alumina and zircoria. The constituents are as the accompanying table.

| Constituent | Addition amount (g) |
| --- | --- |
| alumina | 70 |
| zirconia | 45 |
| dispersant | 0.79 |
| binding agent | 10 |
| plasticizer | 12.5 |
| solvent | 50 |

The slurry forming conditions and properties are as follows.

| Properties | Example 1 |
| --- | --- |
| casting rate (cm/min) | 30 |
| blade height (mm) | 1.45 |
| viscosity | 15500 |
| greensheet left end | 0.55 |
| thickness middle | 0.54 |
| (mm) right end | 0.55 |
| appearance inspection | no faults |
| bending or cracking at skim | none |
| bending or cracking at sinter | none |

EXAMPLE 5
Alumina/Alumina Fiber/ Zirconia Sheet Fabrication

For a first mixture, a yttria stabilized zirconia 3Y-TZP was added in a weight ratio of 14% against the entire powder to a solution including a compound solvent formed of methyl ethyl ketone and ethyl alcohol and including a dispersant KD-1, to thereby pulverize and evenly disperse the aggregation. For a second mixture, an alumina powder having more than 99.5% of purity and an average particle diameter of 3 μm was admixed to the first mixture in a weight ratio of 66% against the entire powder. For a third mixture, to the evenly admixed alumina and zirconia there were added an alumina fiber in a weight ratio of 20% against the entire powder to thereby maintain and improve the structure of a first sintering body. For a fourth mixture, to the even slip formed of alumina particles, zirconia particles and alumina fiber there were added poly vinyl butyryl as a binding agent and dibutyral phthalate as a plasticizer.

| Constituents | Addition amount (g) |
| --- | --- |
| alumina | 70 |
| alumina fiber | 20 |
| zirconia | 15.19 |
| dispersant | 0.79 |
| binding agent | 10 |
| plasticizer | 12.5 |
| solvent | 50 |

The forming conditions of slurry after a defoaming process, and its properties are as follows.

| Properties | Example 1 |
| --- | --- |
| casting rate (cm/min) | 30 |
| blade height (mm) | 1.45 |
| viscosity | 14500 |
| greensheet left end | 0.56 |
| thickness middle | 0.56 |
| (mm) right end | 0.55 |
| appearance inspection | no faults |
| bending or cracking at skim | none |
| bending or cracking at sinter | none |

EXAMPLE 6
Spinel Sheet Fabrication

A spinel ($MgO.Al_2O_3$) powder was added to a compound solvent formed of methyl ethyl ketone and ethyl alcohol and to a solution of a dispersant KD-1, to there by pulverize and evenly disperse the aggregation. To the admixture there were added poly vinyl butyryl serving as a binding agent and dibutyryl phthalate serving as a plasticizer.

| Constituents | Addition amount (g) |
| --- | --- |
| spinel | 100 |
| dispersant | 0.79 |
| binding agent | 10 |
| plasticizer | 12.5 |
| solvent | 50 |

The forming conditions of slurry after a defoaming process, and its properties are as follows.

| Properties | Example 1 |
| --- | --- |
| casting rate (cm/min) | 30 |
| blade height (mm) | 1.40 |
| viscosity (cps) | 13000 |
| greensheet left end | 0.52 |
| thickness(rnrn) middle | 0.53 |
| right end | 0.52 |
| appearance inspection | no faults |
| bending and cracking at skim | none |
| bending and cracking at sinter | none |

EXAMPLE 7
Composition Range of a Forming Available Sheet

Other than the preceding examples there was manufactured a sheet formed of a variety of composition ratios in order to ascertain flexion required to manufacture a ceramic artificial crown. A bending test was carried out so see if any cracking occurred and the extent thereof to the bent portions of the manufactured sheets after bending the sheets to 180° under a there most at and humidist at atmosphere was observed. A tensile test was performed to observe a deforming rate and a rupture tensile strength. To observe a property variation in accordance with a ratio of binding agent and plasticizer to alumina in total contents, the ratio of a binding agent to a plasticizer was fixed to 0.4444 and then the sheet properties were observed while changing the ratio of alumina to alumina +binding agent +plasticizer from 0.7 to 0.9. To observe property variations according to an adduct ratio of a binding agent and a plasticizer, the total organic contents were fixed to maintain the alumina content ratio at 0.816, and a ratio of a binding agent to a binding agent and plasticizer were varied from 0.3 to 0.6 to accordingly observe the sheet properties. Through the above observations, a composition system range in which all ceramic jacket fabrication is applicable was determined and the composition range was applied to fabrication of an alumina/zirconia sheet. A rupture strength and maximum strain of the alumina sheet were measured using a tensile test wherein a universal testing machine is employed. A sheet tensile experimental specimen was formed by punching the sheet into a dumbell shape specimen according to ASTM D-638. The dumbell shape specimen was formed to be smooth without any rough portions so that ruptures only occur within a tensile region. A stress strain curve depends on a tensile rate which was therefore maintained at 1 mm/min. Under an optimal composition region determined through the above experiments, the ratio of binding agent to binding agent+plasticizer ranged from 0.35 to 0.55, and the ratio of ceramic powder to ceramic powder+total organic contents ranged from 0.75 to 0.85.

EXAMPLE 8:
Forming of a Sheet and Gypsum Mold Single Structure

A ceramic sheet manufactured with a composition that is within a feasible forming region, was appropriately cut arid enclosed around a gypsum mold to form a joint molding mass comprising a ceramic sheet and a gypsum mold, which was in turn inserted into a rubber bag and de-aired for one minute using a vacuum machine, and then put into a heat hydrostatic pressing machine and pressured at 20 kgf/cm$^2$ for 10 minutes to thereby form an integrated body. Here, before a ceramic sheet is molded on a tooth-shaped gypsum mold, the gypsum mold is heat-processed at a temperature of 100° C. to 200° C. so that water remaining in the gypsum mold is evaporated. In an integrated body that does not employ such a process, protrusions occur due to the partial swelling of the ceramic sheet which has a lower gas penetration in accordance with a vapor pressure generated in the gypsum mold during sintering, and large pores which had been remaining around interfaces with the gypsum mold were observed those portions abutting to the gypsum mold. The gypsum mold and the ceramic sheet were heated up to a temperature of 500° C. at a temperature increase rate of 1° C./min and maintained for one hour and again heated up to 1150° C. at a temperature increase rate of 3° C./min and maintained for two hours and accordingly sintered, thereby completing a ceramic core fabrication.

Although the preferred embodiments of the present invention have been disclosed for illustrative purposes, those skilled in the art will appreciate that various modifications, additions and substitutions are possible, without departing from the scope and spirit of the invention as recited in the accompanying claims.

What is claimed is:

1. A ceramic sheet slurry composition for fabricating an all ceramic jacket crown applicable to an artificial crown, comprising:

a metallic oxide selected from the group consisting of a particle-type alumina, a spinel (MgO.Al$_2$O$_3$), and a mixed powder comprising alumina and zirconia; 0.5 wt. % to 2.0 wt. % of a dispersant against the metallic oxide; 30 wt. % to 90 wt. % of a solvent against the metallic oxide; 5 wt. % to 12 wt. % of a binding agent against the metallic oxide; and 7 wt. % to 17 wt. % of a plasticizer against the metallic oxide.

2. The composition of claim 1 wherein a weight ratio of the metal oxide to a sum amount of the metal oxide, the plasticizer and the binding agent is set at 0.78~0.83:1 and a weight ratio of the binding agent to a sum amount of the binding agent and a plasticizer is set at 0.4~0.5:1.

* * * * *

UNITED STATES PATENT AND TRADEMARK OFFICE
CERTIFICATE OF CORRECTION

PATENT NO.    : 5,975,905
DATED         : November 2, 1999
INVENTOR(S)   : Dae Joon Kim and Myung Hyun Lee It is certified that error appears in the above-identified patent and that said Letters Patent is hereby corrected as shown below:

On the face of the patent in Section [73], please insert:

Assignees.    Korea Institute of Science and Technology
              Seoul, Republic of Korea Myung Bum Lee
              Seoul, Republic of Korea Signed and Sealed this Twenty-ninth Day of August, 2000

Attest:

Q. TODD DICKINSON

Attesting Officer

Director of Patents and Trademarks